United States Patent [19]

Müller et al.

[11] Patent Number: 5,234,554

[45] Date of Patent: Aug. 10, 1993

[54] METHOD OF SEPARATION OF FATTY ALCOHOLS FROM SOLUTIONS COMPRISING ALKYL POLYGLYCOSIDES AND FATTY ALCOHOLS BY DISTILLATION

[75] Inventors: Bernd Müller, Marl; Norbert Ripke, Haltern, both of Fed. Rep. of Germany

[73] Assignee: Huels Aktiengesellschaft, Marl, Fed. Rep. of Germany

[21] Appl. No.: 892,753

[22] Filed: Jun. 3, 1992

[30] Foreign Application Priority Data

Sep. 6, 1991 [DE] Fed. Rep. of Germany ....... 4129587

[51] Int. Cl.⁵ .......................... B01D 1/22; B01D 3/10
[52] U.S. Cl. .......................... 203/89; 159/49; 159/DIG. 10; 159/DIG. 16; 203/91; 536/127
[58] Field of Search .............. 203/89, 91; 159/49, 159/DIG. 10, DIG. 16; 536/124, 18.6, 127

[56] References Cited

U.S. PATENT DOCUMENTS

| | | | |
|---|---|---|---|
| 4,393,203 | 7/1983 | Mao et al. | 159/49 |
| 4,465,828 | 8/1984 | Rau et al. | 536/124 |

FOREIGN PATENT DOCUMENTS

| | | |
|---|---|---|
| 0092876 | 11/1983 | European Pat. Off. |
| 0306651 | 3/1989 | European Pat. Off. |
| 0306652 | 3/1989 | European Pat. Off. |
| 0421187 | 4/1991 | European Pat. Off. |
| 4026809 | 2/1992 | Fed. Rep. of Germany |
| WO 91/04980 | 4/1991 | PCT Int'l Appl. |

OTHER PUBLICATIONS

Weissberger et al. "Distillation" Technique of Organic Chemistry vol. IV, 1965 p. 617.
Lueders, CA 110(7):57999b, 1987.
Wilhelm et al., CA 115(3):29834d, Apr. 4, 1991.
McCurry et al., CA 114(13):122966n, Jul. 12, 1990.
Henry et al., CA 113 (24):214298d, Jan. 11, 1989.
Langdon, William K. CA 103(6):38987k, Apr. 9, 1985.
Klahr et al. CA 95(14):1174292, Jul. 16, 1981.

*Primary Examiner*—Virginia Manoharan
*Attorney, Agent, or Firm*—Oblon, Spivak, McClelland, Maier & Neustadt

[57] ABSTRACT

Fatty alcohols are separated from a solution containing alkyl polyglycosides (APGs) and alcohols, wherein the alcohols and the alkyl groups of the APGs contain 10–18 C atoms and wherein the mean degree of polymerization of the (APGs) is 1.05–1.4 by distilling said solution at 160°–200° C. under a pressure of 0.1–20 hPa in a thin layer evaporator having a Reynolds number of 30–18,000.

6 Claims, No Drawings

METHOD OF SEPARATION OF FATTY ALCOHOLS FROM SOLUTIONS COMPRISING ALKYL POLYGLYCOSIDES AND FATTY ALCOHOLS BY DISTILLATION

BACKGROUND OF THE INVENTION

1. Field of the Invention

The present invention relates to a method of separating fatty alcohols by distillation from solutions comprising alkyl polyglycosides (APGs) and fatty alcohols.

2. Description of the Background

Alkyl polyglycosides are nontoxic and readily degradable surfactants. Therefore they are used as detergents, cleaning agents, emulsifiers, and dispersants. They have the desired interfacial characteristics only if the alkyl groups have at least 8 carbon atoms.

Alkyl polyglycosides with long-chain alkyl groups are generally manufactured by single-stage or multistage syntheses.

A single-stage synthesis is described, e.g., in German Pat. App. No. P 41 01 252.6.

A two-stage method is disclosed, e.g., in Eur. OS 0,306,652, in which first an n-butyl glycoside is prepared by glycosidation of n-butanol, followed by a trans-glycosidation with a long-chain alcohol to produce the desired long-chain APG.

After completion of the reaction, the APGs are present as solutions in long-chain alcohols. The alcohols must then be separated out if a product is desired which yields a clear solution when dissolved in water.

According to Eur. Pat. 0,077,167, the excess alcohol should be removed as soon as possible. During removal of the alcohol, the thermal stress on the reaction products should not be excessive. In fact the reference examples describe the removal of alcohols by distillation in vacuum. The apparatus used for this, and the conditions, are not specified, however.

In Eur. Pat. 0,092,876, fatty alcohols are removed by distillation from solutions comprising alkyl polyglycosides and fatty alcohols using a thin-layer evaporator. For this method, the Reynolds number should be >20,000.

The consequence of the requirement of a high Reynolds number is that in the event of highly viscous products the layer thicknesses must be high and the rpm of the rotor in the thin-layer evaporator must be high. This results in the formation of products by cracking which stain the evaporator, and premature wear of the moving parts. Accordingly, a need continues to exist for a method by which fatty alcohols can be removed by distillation which saves and protects the product even in the case of highly viscous APG solutions.

SUMMARY OF THE INVENTION

Accordingly, one object of the present invention is to provide an improved method of separating fatty alcohols from solutions with APGs by distillation.

Briefly, the object and other objects of the present invention as hereinafter will become more readily apparent can be attained in a method of separating fatty alcohols from a solution comprising alkyl polyglycosides (APGs) and alcohols by distillation, wherein the alcohols and the alkyl groups of the APGs contain 10-18 C atoms and wherein the mean degree of polymerization of the (APGs) is 1.05-1.4 by distilling the solution at a temperature of 160°-200° C. and a pressure of 0.1-20 hPa in a thin layer evaporator having a Reynolds number of 30-18,000.

DETAILED DESCRIPTION OF THE PREFERRED EMBODIMENTS

In the invention the existing problem is solved by separating fatty alcohols from solution in a thin layer evaporator having a Reynolds number of 30-18,000. Surprisingly, a rapid and product-saving distillation can be achieved in the laminar or weakly turbulent range.

The APGs employed in the present invention may be prepared by any of the known methods, e.g.,: a one-stage method, or a two stage method by glycosidation and transglycosidation. The alkyl polyglycosides contain alkyl groups with 10-18 C atoms, preferably 12-16 C atoms. The mean degree of polymerization is 1.05-1.4, preferably 1.2-1.4. The glycoside units may be derived from the likes of glucose, mannose, maltose, or lactose. Suitable fatty alcohols have 10-18 C atoms, preferably 12-16 C atoms. Examples of the alcohols include decanol, dodecanol, tetradecanol, and mixed alcohols. The alkyl groups introduced into the APGs come from these alcohols.

The APG solutions are fed into the evaporator as 10-70%, preferably 20-50% APG solutions in fatty alcohols, and are adjusted in pH to neutral or weakly alkaline solutions. Suitable solutions are obtained, e.g., directly from the reaction of alkyl polyglycosides with the fatty alcohol, or following a subsequent treatment in which readily volatilized components are removed by distillation.

Suitable thin layer evaporators include falling film evaporators. Preferably, however, thin layer evaporators are employed which enable the formation of layer thicknesses which can be adjusted to specific values by rotating-wipers.

The Reynolds number can be measured at the entrance to the thin layer evaporator, as regards the APG solution, or at the outlet of the evaporator as regards the APG melt. Preferably the Reynolds number is in the range 50-12,000.

The fatty alcohols are removed by distillation preferably at 170°-180° C. and a pressure of 0.1-10 hPa.

In the present invention, the fatty alcohols are removed from the APG having a residual content of <2%, at residence times of 15 sec to 2 min. The method enables distillation at high vacuum and relatively low temperatures. The result is clear APGs which give clear aqueous solutions. Because of the low Reynolds number, foam formation is low, and consequently formation of solid deposits in the thin layer evaporator is low.

Having now generally described this invention, a further understanding can be obtained by reference to certain specific examples which are provided herein for purposes of illustration only and are not intended to be limiting unless otherwise specified.

In the following Examples, neutralized solutions comprising APGs and fatty alcohols are used wherein the alkyl groups of the APGs correspond to the alkyl groups of the alcohols.

The Reynolds number is determined from the formula $$Re = \frac{\delta \cdot u \cdot d}{\eta}$$

where δ represents density, u represents rotational speed, d represents gap thickness, and η represents viscosity.

EXAMPLE 1

A neutralized 25% solution of APGs (mean degree of polymerization=1.4) in a mixture of alcohols comprised of decanol (<1.5%), dodecanol (c. 68%), tetradecanol (c. 27%), hexadecanol (<6%), and octadecanol (<0.5%) (Nafol® 1214 Z, supplied by the firm Condea, D-2212 Brunsbuettel, Germany) was fed to a thin layer evaporator. The solution at 170° C. had a density of 777 kg/m$^3$ and a viscosity of 3 mPa-sec.

The alcohol mixture was removed by distillation in the evaporator at 170° C. and a pressure of 1 hPa. The wiper of the evaporator had a rotational speed of 8.4 m/sec. The gap thickness was 0.0015 m.

A light-colored product was obtained which at 170° C. had a density of 1,034 kg/m$^3$ and a viscosity of 190 mPa-sec. The residual alcohol content was <1%.

The Reynolds number at the inlet of the evaporator was 3,263, and that at the outlet of the evaporator was 69.

EXAMPLE 2

The APG solution of Example 1 was fed to a thin layer evaporator operated at 180° C., 1 hPa, a wiper speed of 8.4 m/sec, and a gap thickness of 0.001 m.

At 180° C. the solution employed had a density of 769 kg/m$^3$ and a viscosity of 2 mPa-sec. A light colored APG was obtained which had a residual alcohol content of <1%. The Reynolds number at the inlet of the evaporator was 3,230.

EXAMPLE 3

A neutralized 25% solution of APGs (mean degree of polymerization=1.4) in a mixture of alcohols comprised of decanol (<2%), dodecanol (c. 70%), tetradecanol (c. 27%), and hexadecanol (<1.5%), (Nafol® 1214 S) was fed to a thin layer evaporator. The solution at 180° C. had a density of 730 kg/m$^3$ and a viscosity of 0.9 mPa-sec.

The alcohol mixture was removed by distillation in the evaporator at 180° C. and a pressure of 1 hPa. The wiper of the evaporator had a rotational speed of 8.4 m/sec. The gap thickness was 0.0025 m.

An APG was obtained which had a residual alcohol content of <1%.

The Reynolds number at the inlet of the thin layer evaporator was 17,033.

EXAMPLE 4

A neutralized 25% solution of APGs (mean degree of polymerization=1.3) in the alcohol mixture of Example 1 was fed to a thin layer evaporator.

The evaporator was operated at 180° C., 1 hPa, a wiper speed of 8.4 m/sec, and a gap thickness of 0.0015 m.

The product at the outlet of the evaporator had, at 180° C. a density of 1,025 kg/m$^3$ and a viscosity of 110 mPa-sec. Its residual alcohol content was <1%. The Reynolds number at the outlet of the thin layer evaporator was 117.

Having now fully described the invention, it will be apparent to one of ordinary skill in the art that many changes and modifications can be made thereto without departing from the spirit or scope of the invention as set forth herein.

What is claimed as new and described to be secured by Letters Patent of the United States is:

1. A method consisting essentially of separating fatty alcohols from a solution including alkyl polyglycosides (APGs) and alcohols, wherein the alcohols and the alkyl groups of the APGs contain 10–18 C atoms and wherein the mean degree of polymerization of the (APGs) is 1.05–1.4; distilling said solution at a temperature of 160°–200° C. and pressure of 0.1–20 hPa in a thin layer evaporator having a Reynolds number of 30–18,000.

2. The method according to claim 1, wherein said solution is a 10–70% solution of APGs in alcohols.

3. The method according to claim 1, wherein the alcohols and the alkyl groups of the APGs contain 12–16 C atoms.

4. The method according to claim 1, wherein the APGs have a mean degree of polymerization of 1.2–1.4.

5. The method according to claim 1, wherein the distillation is carried out at Reynolds numbers of 50–12,000.

6. The method according to claim 2, wherein said solution is a 20–50% solution of APGs in alcohols.

* * * * *